United States Patent [19]

Amin et al.

[11] Patent Number: 4,902,683

[45] Date of Patent: Feb. 20, 1990

[54] CRYSTALLINE CEPHALOSPORIN HYDROHALIDE SALTS

[75] Inventors: Mahendra I. Amin, Kalamazoo; Jay A. Campbell, Portage, both of Mich.

[73] Assignee: The Upjohn Company, Kalamazoo, Mich.

[21] Appl. No.: 312,401

[22] Filed: Feb. 17, 1989

Related U.S. Application Data

[63] Continuation of Ser. No. 898,676, Aug. 21, 1986, abandoned, which is a continuation of Ser. No. 664,651, Oct. 25, 1984, abandoned.

[51] Int. Cl.$^4$ .................. C07D 501/36; A61K 31/545
[52] U.S. Cl. .................................... 514/206; 540/227
[58] Field of Search .......................... 540/227; 514/206

[56] References Cited

U.S. PATENT DOCUMENTS 4,464,367  8/1984  Labeeuw et al. .................. 540/227

FOREIGN PATENT DOCUMENTS 2036746A  7/1980  United Kingdom .

*Primary Examiner*—Nicholas S. Rizzo
*Attorney, Agent, or Firm*—Martha A. Cox

[57] ABSTRACT

Crystalline hydrohalide salts of the cephalosporin antibiotic ceftiofur, processes for their manufacture, and pharmaceutical compositions containing one of these salts are provided.

13 Claims, No Drawings

CRYSTALLINE CEPHALOSPORIN HYDROHALIDE SALTS

This is a continuation of U.S. patent application Ser. No. 898,676 filed Aug. 12, 1986 now abandoned which is a continuation-in-part of U.S. patent application Ser. No. 664,651 filed Oct. 25, 1984, now abandoned.

INTRODUCTION

This invention relates to a new crystalline hydrochloride salt form of a cephalosporin antibiotic and to a process for preparing the crystalline cephalosporin hydrochloride salt substantially free of impurities, and pharmaceutical compositions and methods of use therefor.

BACKGROUND OF THE INVENTION

The cephalosporin antibiotic 7-[2-(2-amino-1,3-thiazol-4-yl)-2-methoxyimino)acetamido]-3-[(fur-2-ylcarbonyl)thiomethyl]-3-cephem-4-carboxylic acid (also named 7-[2-(2-amino-4-thiazolyl)-2-methoxyimino)-acetamido]-3-[2-(furanylcarbonylthiomethyl)-8-oxo-5-thia-1-azabicyclo[4.2.0]oct-2-ene-1-carboxylic acid) (2), its alkali metal, alkaline earth metal and amine salts of the carboxylic acid group, and easily hydrolyzable ester groups thereof are described and claimed in Labeeuw et al U.S. Pat. No. 4,464,367. This cephalosporin free acid (2) compound is now known by the generic name ceftiofur, in France.

Those free acid and cationic metal and amine salt and ester forms of this cephalosporin antibiotic are somewhat unstable chemically and are obtained as amorphous compounds which are difficult to purify, and are less desirable to work with in manufacturing pharmaceutical formulations containing them. Those patented salts thus create salt-solid-isolation and salt-solid-handling problems in a pharmaceutical manufacturing plant which those in the pharmaceutical art would prefer to avoid. However, it is not predictable how to make useful crystalline salt forms of any particular active drug cephalosporin compound.

OBJECTS OF THE INVENTION

It is an object of the invention to provide a useful crystalline salt form of the above new cephalosporin compound having advantageous solubility and other physical properties, which make the compound easier to purify and more convenient to work with in preparing pharmaceutical formulation composition dosage forms thereof.

It is another object of this invention to provide a process for purifying and isolating the above cephalosporin compound as its crystalline hydrohalide salt form to obtain the cephalosporin hydrohalide salt in a degree of purification which is not possible when the amorphous solid forms of the cephalosporin are obtained and processed.

It is another object of this invention to provide pharmaceutical compositions containing the new crystalline ceftiofur hydrohalide salt of this invention.

SUMMARY OF THE INVENTION

This invention provides a crystalline hydrohalide salt (1) of 7-(2-amino-1,3-thiazol-4-yl)-2-methoxyimino)acetamido]-3-[(fur-2-ylcarbonyl)thiomethyl]-8-oxo-5-thia-1-azabicyclo[4.2.1]oct-2-ene-1-carboxylic acid (2), ceftiofur, in a form which is easier to isolate, purify and to handle in subsequent pharmaceutical operations, and pharmaceutical composition thereof.

The salt forming and purification process of this invention comprises (a) treating the N-tritylamino cephalosporin (3) with a solution containing a water-miscible organic solvent such as acetone, tetrahydrofuran, acetonitrile, or methyl ethyl ketone, preferably acetone, water and hydrogen halide which is at least stoichiometrically equivalent to the amount of the N-tritylamino cephalosporin (3), (b) heating the mixture from step (a) to a temperature and for a time sufficient to effect detritylation, (c) decreasing the concentration of the water miscible organic solvent in the aqueous phase of the mixture from step (b) to effect formation of the crystalline cephalosporin hydrohalide salt (1), for example, by adding to the mixture a non-polar, water immiscible organic liquid, e.g., toluene or heptane, to extract the water-miscible solvent, e.g., acetone, and to take up the trityl alcohol by-product, or by distillation of the mixture to separate some of the water miscible organic solvent, e.g., acetone, or by other physical or chemical means, and also, optionally by adding water and hydrogen halide to enhance crystal salt formation, (d) recovering the crystalline cephalosporin hydrohalide salt (1) from the liquid mixture from step (c);

(e) washing the crystalline cephalosporin hydrohalide salt (1) from step (d) with water and water-miscible organic solvent, and (f) drying the washed crystalline cephalosporin hydrohalide salt from step (e).

This cephalosporin hydrohalide salt (1) can also be prepared from the cephalosporin amino-acid (2) or from other alkali metal, alkaline earth metal or amine salts such as (4) by treating a solution of the cephalosporin compound in an aqueous/organic liquid mixture solution, e.g., an aqueous/acetone mixture, with the hydrogen halide. The crystalline cephalosporin hydrohalide salt (1) is then precipitated by either removing some of the organic liquid, e.g., acetone, or by removing the aqueous phase from the mixture, either of which actions cause the crystalline cephalosporin hydrohalide salt (1) to precipitate, which crystalline precipitate can then be recovered from its liquid mixture by known means.

DETAILED DESCRIPTION OF THE INVENTION

This invention provides a crystalline form of a cephalosporin antibiotic as its hydrohalide salt (see attached STRUCTURE SHEET) of Formula 1 where X is chloride or bromide. As a matter of economics the hydrochloride salt is preferred, although the hydrobromide salt can be made and used in a similar manner. As indicated above the cephalosporin antibiotic can be named by either of two above different nomenclature systems. Some persons prefer the more formal CHEMICAL ABSTRACTS system wherby the compound is named as a derivative of a "bicyclo" ring system. Some prefer the simpler "cephem" ring system nomenclature.

This crystalline hydrochloride salt of structure (1) where X is chloride has the following x-ray powder diffraction pattern when crystallized from water-acetone.

| interplanar d-spacings Å | intensity (relative %) |
| --- | --- |
| 18.4 | 44.2 |
| 12.4 | 73.1 |
| 8.26 | 50.0 |
| 7.82 | 100.0 |
| 7.69 | 17.9 |
| 6.19 | 48.1 |
| 5.86 | 32.1 |
| 5.21 | 23.1 |
| 5.12 | 40.4 |
| 4.74 | 30.1 |
| 4.37 | 21.8 |
| 4.23 | 13.5 |
| 3.98 | 26.9 |
| 3.91 | 35.9 |
| 3.81 | 17.9 |
| 3.30 | 14.1 |
| 3.01 | 12.8 |
| 2.88 | 14.1 |

(Peaks with relative intensity equal to or less than 10% are not reported.)

The salt may contain 0.5 to 2.0 equivalents of hydrogen chloride, but most often around one equivalent of HCl.

The crystalline hydrochloride salt can be crystallized in a solvent consisting of a polar organic solvent or water or a mixture of such solvents. A typical crystallization involves slurrying one gram free acid (2) in 20 ml. of 3% V/V water in acetone at 25° C. At least two equivalents of hydrogen chloride are added to dissolve the free acid and crystallize the hydrochloride salt. The crystals can be separated by filtration and washed to remove the remaining mother liquid. The crystals may then be dried under vacuum at elevated temperature. The yields of hydrochloride salt are generally 60% to 95% depending on the solvent and the purity of the free acid (2).

This salt may contain 0.5% to 7% of water or other solvents (usually 1%–3%). Other impurities are usually reduced to 1% or less.

A recrystallization may be performed by either (a) forming and isolating the free acid (2) and then reforming the hydrochloride salt (1) or (b) by dissolving the hydrochloride salt (1) in aqueous organic solvent (usually containing one or more equivalents of HCl) and then removing the organic solvent by distillation, extraction, or other method of separation.

The free acid (2) or other pharmaceutically acceptable salts (such as (4)) can be made from the purified hydrochloride salt.

Other crystallization solvents include acetonitrile, tetrahydrofuran, methyl ethyl ketone and water. The hydrobromide salt can be made by a similar procedure.

The hydrochloride salt can also be made directly from the tritylprotected cephalosporin. For example, the crude trityl cephalosporin is slurried in 37% V/V water in acetone. Three equivalents of hydrogen chloride are added and the solution is refluxed until detritylation is complete. Toluene or equivalent non-polar water immiscible organic liquid solvent is added while stirring. The mixture is allowed to separate and the aqueous phase is removed and cooled to crystallize the hydrochloride salt. See Example 4 hereinbelow.

In aqueous buffer solutions the sodium salt (Formula 4) is more stable as the pH decreases. In hydrochloric acid at pH values equal to or lower than 2.8 the sodium salt (4) is converted to the hydrochloride salt (1) which exhibits better shelf stability when it is separated, washed and dried.

The new hydrochloride salt (1) has lower aqueous solubility than the sodium salt (4) and the free acid (2), and is better adapted for making controlled release pharmaceutical dosage formulations such as oral and parenteral suspensions, suppository and tablet dosage forms.

The new hydrochloride salt (1) produces acceptable pharmaceutical dispersions in water for injection and in pharmaceutical vegetable oils. Due to this property, the hydrochloride salt (1) can be formulated into extemporaneous (liquid and drug powder mixed just prior to administration) liquid suspensions by the addition of an aqueous or an oily vehicle to the hydrochloride salt (I) powder, just prior to dosing the patient. Oral and subcutaneous studies in mice with aqueous and oil dispersions of both the hydrochloride (1) and the sodium salt (4) indicate that the hydrochloride (1) is bioequivalent to the sodium salt (4). However, we have found that the crystalline hydrochloride salt (1) can be made in more pure form, is easier and is less expensive to manufacture than the sodium salt (4). Further, since the hydrochloride (1) has more limited solubility in water various controlled release pharmaceutical dosage formulations can be made with it (1) that are not readily adaptable to the sodium salt (4).

Due to the lower solubility of the ceftiofur hydrochloride, its rate of dissolution is slower. As a result absorption is less, and thus various controlled release formulation(s) can be formulated.

The controlled release parenteral suspension (see Examples 12 and 14 below) can be given once every 2 to 5 days as opposed to being given daily with other formulations.

The invention, how to make it and how to use it are further exemplified by the following detailed examples which are not intended to be limiting. In these examples, "povidone" is a known form of polyvinylpyrrolidone, used in pharmacy. "Quatresin" is a brand name for myristyl gamma-picolinium chloride. The corn oil glycerol monostearate gel and cottonseed oil glycerol monostearate gel materials are described in U.S. Pat. No. 4,034,099. "Suppocire" refers to a brand name of a series of mixtures of saturated glycerides of $C_{10}$ to $C_{18}$-fatty acids which are known in pharmacy as excipients for use in various suppository and other pharmaceutical formulations and are described in product bulletins of Gatte fosse Establissment SA., Paris, France, 39 Avenue Edouard-Vaillant: "Suppocire AM" is said to have a melting point of 35° C. to 36.5° C. PEG-400 and PEG-8000 are well known pharmaceutical excipient forms based upon polyethylene glycol. Carnauba wax is the pharmaceutical form thereof defined in the National Formulary (NF).

The improved hydrohalide salt forming and purification process of this invention is adaptable to and can be used with a proposed large scale process for making the cephalosporin compound itself.

The N-trityl cephalosporin derivative (3) which is the preferred starting material is prepared by acylation of the corresponding 7-amino precursor 3-cephem-4-carboxylic acid nucleus compound with the N-trityl-2-amino-1,3-thiazol-4-yl-2-methoxyimino acetic acid by acylation methods well known to those skilled in the cephalosporin production art. For example, the procedure described in U.S. Pat. No. 4,464,367 for the preparation of (3) with N-hydroxybenzotriazole and N,N- dicyclohexylcarbodiimide can be used. Alternately, the corresponding acid chloride can be prepared and used as described in the *Journal of Antibiotics*, 36, 180 (1983).

According to the process of this invention in step (a) the N-trityl-cephalosporin (3) (see STRUCTURE SHEET) is treated with a solution mixture of a polar solvent (e.g., acetone) and water (in proportions ranging from about 200 to 100 parts V/V of polar solvent per 100 parts of water) in an amount to obtain a workable slurry. Sufficient hydrogen halide (e.g., hydrogen chloride) is then added. The hydrogen halide can be added in an amount which is at least stoichiometrically equivalent to the trityl-amino compound (3). For efficiency reasons, we prefer to add about three equivalents of hydrogen halide per equivalent of the trityl-protected cephalosporin (3). The hydrogen halide can be added as a gas, below the liquid surface, or as a hydrohalic acid solution in water.

In step (b), the acidified mixture from step (a) is heated to a temperature, generally above 45° C., and for a time sufficient to effect detritylation of the cephalosporin (3) and to form the cephalosporin hydrohalide salt (1). We have found that reflux of the mixture, which occurs in our mixtures at about 56° C., for about one hour is sufficient to effect the detritylation, without destruction of the cephalosporin.

In step (c) of the process the detritylated cephalosporin hydrohalide mixture is washed with a non-polar non-water miscible organic liquid which liquid takes up the trityl alcohol by-product and some of the acetone in the mixture. Examples of useful liquids for this purpose include liquid aromatic hydrocarbons such as benzene, toluene, xylene, chlorinated aromatic hydrocarbons such as chlorinated benzene, toluene and xylene, and chlorinated alkanes such as methylene chloride, dichloroethane, chloroform, carbon tetrachloride, as well as $C_2$ to $C_3$-alkyl acetate and propionate esters such as ethyl acetate, propyl acetate and liquid $C_6$ to $C_{10}$-alkanes such as hexanes, heptane, octane, nonane and decane, and liquid $C_5$ to $C_7$-cycloalkanes such as cyclopentane, cyclohexane, cycloheptane, and mixtures, including commercial mixtures of such liquids. Toluene and/or heptane are preferred. Optionally, extra water and acid may also be added at this point. The hydrohalic acid addition is optional because it depends upon the amount of hydrogen halide already present in the mixture. The added hydrogen halide at this stage gives shorter cyrstallization times.

In step (d) the crystalline cephalosporin hydrohalide salt (1) is separated from the liquid phase by known means such as by filtration or centrifugation procedures, and in step (e) the separated crystalline cephalosporin hydrohalide salt (1) is washed one or more times with water and water-miscible organic solvent, e.g., acetone, or mixtures thereof, and then dried (step f), for example, by spreading the crystalline salt in trays, and drying the salt in a vacuum oven at 40°-60° C. for a time sufficient to remove any adhering volatile liquids therefrom.

The compounds of Formula 1 herein are useful as the active antibiotic drug compound in pharmaceutical dosage forms for treating valuable mammalian animals and humans to treat bacterial infections in that valuable animal or human. Presently it is contemplated that this compound will be especially useful as a veterinary antibiotic drug to treat valuable animals such as cattle, horses, goats, dogs and cats to fight the effects of bacterial infections caused by organisms such as *Pasturella hemolitica, Salmonella typhimurium, E. coli, Staphylococcus, aureus*, and the like, some of which are commonly associated with 'shipping fever' in animals.

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification. Examples of suitable dosage unit forms in accordance with this invention are tablets, capsules, orally administered liquid preparations in suitable liquid vehicles, sterile preparations in suitable liquid vehicles for intramuscular and intravenous administration, suppositories and sterile dry preparations for the extemporaneous preparation (mixing just prior to administration) of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of this antibiotic active ingredient in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, alginates, tragacanth, pectin, kelgin, carragenan, acacia, polyvinylpyrrolidone, polyvinyl alcohol, and the like, to increase the viscosity of the composition. In the case of injectable forms, the injectable formulation must be sterile and must be fluid to the extent that easy syringeability exists. Such preparations must be stable under the conditions of manufacture and storage, and ordinarily contain in addition to the principal solvent or suspending liquid, preservatives in the nature of bacteriostatic and fungistatic agents, for example, parabens, chlorobutanol, benzyl alcohol, benzoic acid, phenol, thimerosal, and the like to preserve the composition against microorganisms. In many cases, it is preferable to include osmotically active agents, for example, sugars or sodium chloride in isotonic concentrations. Carriers and vehicles include vegetable oils, dimethylacetamide, dimethylformamaide, ethyl lactate, ethyl carbonate, isopropyl myristate, ethanol, polyols, for example, glycerol, propylene glycol, liquid polyethylene glycol, and the like. Any solid preparations for subsequent extemporaneous preparation of sterile injectable preparations are sterilized, by exposure to steam, cobalt 60 irradiation, or by exposure to a sterilizing gas, for example, ethylene oxide. The aforesaid carriers, vehicles, diluents, surfactants, excipients, preservatives, isotonic agents and the like constitute the pharmaceutical means which adapt the preparations for systemic administration.

In these pharmaceutical compositions it may be desirable to include a viscosity increasing agent such as sodium carboxymethylcellulose (sodium CMC). Other suitable viscosity increasing agents can be substituted for sodium CMC.

The pharmaceutical dosage unit forms of the compounds of this invention are prepared in accordance with the preceding general description to provide from about 1 mg. to about 500 mg. of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain antibiotic effects within the aforesaid effective non-toxic range. Expressed otherwise, when used systemically, an amount of the essential active ingredient is provided to a recipient within a range from about 0.2 mg./kg. to about 10 mg./kg. of body weight of the recipient.

Preferred dosages for most applications are 0.2 mg./kg. to 5.0 mg./kg. of body weight. In a topical semi-solid ointment formulation the concentration of the active ingredient may be 1%–20%, preferably 5%–10% in a carrier, such as a pharmaceutical cream base.

The useful pharmaceutical dosage unit forms of these compounds in pharmaceutical formulations are preferably adapted for systemic administration to obtain antibiotic effects comprising an effective, non-toxic amount of the Formula 1 salt.

Further, the invention relates to methods of obtaining antibiotic effects in mammals, for example, humans and valuable warm-blooded animals such as dogs, cats, horses, and other commercially valuable animals, by administering systemically to the mammals the aforesaid pharmaceutical dosage units forms supplying an effective, non-toxic amount for antibiotic effects.

The invention is further illustrated by the following detailed examples.

EXAMPLE 1

A slurry of 0.7 g. of ceftiofur as its free acid in 7 ml. of acetone and 0.35 ml. of water is made up. To this slurry is added 0.24 ml. of 37.7% hydrochloric acid solution. The resulting acidified slurry becomes a solution within a minute, and then crystallization of the ceftiofur hydrochloride salt begins within 2 or 3 minutes. An additional 7 ml. of acetone are added to thin the slurry. The slurry mixture is stirred for 10 minutes at 20° C. and then filtered and the filtered hydrochloride salt crystals are washed with acetone. The ceftiofur hydrochloride salt crystals are then dried for 16 hours in a vacuum oven. The yield of the ceftiofur hydrochloride salt crystals is 0.63 g., for an 84% chemical yield.

EXAMPLE 2

A slurry of 0.7 g. of ceftiofur free acid in 11.8 ml. of acetone and 6.9 ml. of water is made up. To this slurry there is added 0.27 ml. of 37.7% hydrochloric acid solution, and the mixture is warmed to 55° C. The ceftiofur free acid is in solution. To this warmed solution a 55° C. temperature mixture of 13.2 ml. of toluene and 3.2 ml. of water is added while stirring. The liquid phases are allowed to separate, and the upper organic layer is discarded. The lower aqueous layer is cooled to 15° C. after seeding with previous crystalline ceftiofur hydrochloride, and allowed to stand for two hours. After standing, the mixture is filtered to separate the crystalline ceftiofur hydrochloride salt from the liquid mother liquor. The filtered salt crystals are washed with 4 ml. of 20% acetone in water V/V mixture. Then the salt crystals are washed with 10 ml. of water. The washed ceftiofur hydrochloride salt crystals are dried for 16 hours in a vacuum oven at 40° C. The yield of ceftiofur hydrochloride salt crystals is 0.50 g. for a 67% chemical yield.

EXAMPLE 3

Detritylation of N-trityl-ceftiofur and Crystallization of Ceftiofur Hydrochloride Salt Using Toluene Extraction of Acetone To a three-necked, round-bottom 250 ml. flask is charged 14.8 g. of N-tritylated ceftiofur free acid (3), 91 ml. of acetone, 2.4 ml. of concentrated hydrochloric acid and 91 ml. of water. This resulting mixture is heated to reflux. Then 10 ml. more of acetone is added to dissolve a precipitate, presumably trityl alcohol.

While the mixture is still hot (55° C.), 60 ml. of toluene is added to remove trityl alcohol and to decrease the concentration of acetone in the aqueous phase. The resulting mixture is transferred to a separatory funnel and the liquid layers are separated. The organic liquid phase is washed with a mixture of 25 ml. of water and 10 ml. of acetone. The organic layer is 120 ml. total volume. The separated aqueous layer is washed with 30 ml. of toluene, and then the toluene and aqueous phases are separated to give a 45 ml. total volume toluene plus inter-phase. The aqueous layer (about 140 to 150 ml.) is stirred with a magnetic stir bar for three hours, and then cooled to −5° C. and filtered to separate the ceftiofur hydrochloride salt crystals which form. This crystalline filtered salt product is washed with 15 ml. of a mixture consisting of 10 ml. of water and 5 ml. of acetone. The washed ceftiofur hydrochloride crystalline product, 4.63 g., is dried at 50° C.

A second crop can be obtained by filtering mother liquor filtrate. The resulting ceftiofur hydrochloride crystalline product, 1.46 g., is washed with water. The total yield is 88.1%.

EXAMPLE 4

A mixture of 96 ml. acetone, 55 ml. water and 2.93 ml. 37.7% HCl in water solution are added to about 10.0 gm. trityl cephalosporin (3) and refluxed (about 58° C.) for one hour to affect detritylation.

A mixture of 18 ml. heptane and 4.5 ml. acetone is added to the above solution. The combined liquids are transferred to a separatory funnel and allowed to separate. The lower layer (aqueous) is transferred to another separatory funnel and 18 ml. of heptane and 4.5 ml. of acetone are added to the aqueous phase in the second separatory funnel. The combined liquids are contacted and allowed to separate as before. The lower phase (aqueous) is distilled atmospherically to a temperature of 67° C. which reduces the concentration of acetone to about 15%. Before cooling to 15° C., 2.93 ml. of 37.7% HCl solution are added. The cephalosporin HCl salt (1) begins crystallizing between 50° C. and 60° C.

The crystals are filtered and washed with 20 ml. of 10% acetone in water to remove any adhering filtrate. The resulting washed, filtered solids are then washed with water and dried in a vacuum oven at 65° C. to give 6.87 g. of product.

EXAMPLE 5

Oral Suspension

One thousand cc. of an aqueous suspension for oral use, containing in each 5 cc. dose 5 to 300 mg. of crystalline ceftiofur hydrochloride is prepared from the following types of and amounts of ingredients.

Ceftiofur hydrochloride (crystalline): 5 to 300 gms.
Benzoic Acid or Sorbic Acid: 1 gm.
Sucrose: 650 gms.
Sodium Carboxymethylcellulose, Low Viscosity: 1 to 20 gms.
Flavors (e.g., USP cherry, orange) q.s.
Sodium Chloride (0.5 to 10 mg./ml.): 0.5 to 10 gms.
Hydrochloric Acid, Reagent Grade: q.s. adjust pH to approx. 3.0
Deionized Water: q.s. to 1000 cc.

The sodium carboxymethylcellulose, benzoic acid, sucrose, appropriate flavors and sodium chloride are dispersed in sufficient water to make 650 mls. of solution. The ceftiofur hydrochloride is stirred into the syrup until uniformly distributed. The resulting suspension is colloid milled to a uniform consistency. Sufficient water is added to bring volume to 900 cc. If necessary pH is adjusted with hydrochloric acid to about pH3. Sufficient water is added to make 1000 cc.

EXAMPLE 6

Sterile Parenteral Suspension

Sterile Vehicle-Part I

PEG: 5 to 120 gms.
Benzyl Alcohol, or: 9.1 gm.
Benzoic Acid: 1.0 gm.
Povidone: 1 to 10 gms.
Sodium Chloride Fine Crystals, Reagent Grade: 9 gms.
Hydrochloric Acid, Reagent Grade q.s. adjust pH to approximately: 3.0
50% Solution Sodium Hydroxide q.s. adjust pH:
Water for Injection q.s. adjust: 1000 cc.

Part II

Ceftiofur hydrochloride, crystalline: 1.0 to 100 gms.
Vehicle Part I q.s. adjust: 1000 cc.

DIRECTIONS

Part I

All of the ingredients are dissolved in water and pH adjusted to about 2.6 to 3.2, preferably about 3.0. The vehicle sterilized by filtration and used in Part II.

Part II

Aseptically add sterile crystalline ceftiofur hydrochloride in sufficient vehicle from Part I to make 900 mls. Stir the suspension and colloid mill the suspension to a uniform consistency. Add sufficient vehicle to make 1000 mls.

EXAMPLE 7

Sterile Parenteral Suspension

Sterile Vehicle-Part I

Polysorbate 80, N.F.: 0.1 to 10 gms.
Sodium Carboxymethylcellulose low viscosity: 2 to 20 gms.
Benzyl Alcohol: 9.1 gms.
Benzoic Acid: 0.2 to 2.0 gms.
Povidone: 1 to 10 gms.
Sodium Chloride, Fine Crystals Reagent if needed: 9 gms.
Hydrochloric Acid, Reagent Grade q.s. adjust pH to approx.: 3.0
50% Solution Sodium Hydroxide q.s. adjust pH:
Water for Injection q.s. adjust: 1000 cc.

Part II

Ceftiofur hydrochloride, crystalline: 1.0 to 100 gms.
Vehicle Part I q.s. adjust: 1000 cc.

DIRECTIONS

Part I

All of the ingredients are dissolved in water and the vehicle sterilized by filtration.

Part II

Aseptically add sterile crystalline ceftiofur in sufficient vehicle to make 900 mls. Stir the suspension and pass through colloid mill to a uniform consistency. Add sufficient vehicle to make 1000 mls.

EXAMPLE 8

Sterile Parenteral Suspension

Sterile Vehicle-Part I

PEG 3350 NF: 5 to 120 gms.
Benzyl Alcohol: 9.1 gms.
Benzoic Acid: 0.2 to 2.0 gms.
Polysorbate 80 NF Food Grade: 1 to 5 gms.
Sodium Chloride Fine Crystals Reagent: 0.5 to 10 gms.
Hydrochloric Acid, Reagent Grade q.s. adjust pH to approx.: 3.0
50% Solution Sodium Hydroxide q.s. adjust pH:
Water for Injection q.s. adjust: 1000 cc.

Part II

Ceftiofur hydrochloride, crystalline: 1 to 100 gms.
Vehicle Part I q.s. adjust: 1000 cc.

DIRECTIONS

Part I

All of the ingredients are dissolved in water and pH adjusted to approximately 3.0, and the vehicle sterilized by filtration.

Part II

Aseptically add sterile crystalline ceftiofur hydrochloride in sufficient vehicle from Part I to make 900 mls. Stir the suspension and pass through a colloid mill to a uniform consistency. Add sufficient vehicle to make 1000 mls.

EXAMPLE 9

Sterile Extemporaneous Parenteral Suspension (Aqueous)

Sterile Vehicle-Part I

Benzyl Alcohol or: 9.1 gms. or
Benzoic Acid: 0.2 to 2.0 gms.
Carboxymethylcellulose Sodium USP: 1.0 to 20.0 gms. low viscosity or any other viscosity:
inducing agent:
Sodium Chloride Fine Crystals, Reagent Grade: 0.5 to 10 gms.

Hydrochloric Acid, Reagent Grade q.s. adjust pH to approx.: 3.0
Water for Injection

| Part II | Amount per Vial |
|---|---|
| Sterile Crystalline ceftiofur, hydrochloride in a 10 to 100 ml. glass vial | 0.01 to 1.5 gm. |

DIRECTIONS

Part I

All of the ingredients are dissolved in water, and pH adjusted to approximately 2.6 to 3.2, preferably about 3.0. Vehicle sterilized by filtration and packaged in appropriate glass vials.

Part II

Sterile crystalline ceftiofur hydrochloride is packaged aseptically in sterile vials or crystalline ceftiofur hydrochloride is first packaged and the final container(s) sterilized by Cobalt 60 irradiation.

EXAMPLE 10

Sterile Extemporaneous Parenteral Suspension

Sterile Vehicle Part I

Methylparaben: 1.0 to 2.7 gms.
Propylparaben: 0.1 to 0.5 gm.
Povidone: 1 to 10 gms.
Sodium Chloride Fine Crystals Reagent Grade: 0.5 to 10 gms.
20% Solution Hydrochloric acid q.s. adjust pH to approx.: 3.0
50% Solution Sodium Hydroxide q.s. adjust pH
Water for Injection q.s. adjust: 1000 ccs.

| Part II | Amount per Vial |
|---|---|
| Sterile crystalline ceftiofur hydrochloride in a 10 to 100 ml. glass vial | 0.01 to 1.5 gm. |

DIRECTIONS

Part I

Methylparaben and propylparaben are dissolved in boiling water. Then all of the ingredients dissolved in water, and pH adjusted to approximately 2.6 to 3.2, preferably about 3.0. Vehicle sterilized by filtration and packaged in appropriate glass vials.

Part II

Sterile crystalline ceftiofur hydrochloride is packaged aseptically in sterile vials or crystalline ceftiofur hydrochloride is first packaged and the final container(s) shall be sterilized by Cobalt 60 irradiation.

EXAMPLE 11

Extemporaneous Parenteral Suspension (Aqueous)

Sterile Vehicle-Part I

Polyethylene Glycol 3350 NF: 5 to 120 gms.
Polyvinyl Pyrrolidone: 1 to 10 gms.
Quatresin ® myristyl gamma picolinium chloride: 0.1 to 2.0 gms.
Sodium Chloride, Fine Crystals Reagent Grade: 0.5 to 10 gms.
20% Solution Hydrochloric Acid q.s. adjust pH to approx.: 3.0
50% Solution Sodium Hydroxide q.s. to adjust pH to approx.: 3.0
Water for Injection q.s. adjust to: 1000 cc.

| Part II | Amount per Vial |
|---|---|
| Sterile crystalline ceftiofur hydrochloride (milled or micronized) in a 10 to 100 ml. glass vial | 0.01 to 1.5 gms. |

DIRECTIONS

Part I

All of the ingredients are dissolved in water, and pH adjusted to approximately 2.6 to 3.2, preferably about 3.0. Vehicle sterilized by filtration and packaged in appropriate glass vials.

Part II

Sterile crystalline ceftiofur hydrochloride is packaged aseptically in sterile vials or crystalline ceftiofur hydrochloride is first packaged and the final container(s) are sterilized by Cobalt 60 irradiation.

EXAMPLE 12

Sterile Nonaqueous Parenteral Suspension

Crystalline ceftiofur hydrochloride (milled or micronized): 1 to 100 gms.
Chlorobutanol Anhydrous-preservative: 5.25 gms.
or:
Benzyl Alcohol: 9.25 gms.
Corn Oil Glyceryl Monostearate Gel
or
Cottonseed Oil Glyceryl Monostearate Gel: q.s. adjust

DIRECTIONS

Preservative is dissolved in sufficient oily gel to make 800 cc. Crystalline ceftiofur hydrochloride is added, and the suspension is colloid milled to a uniform consistency. Add sufficient gel to make 1000 mls. After packaging into glass vials, the suspension is sterilized by Cobalt 60 irradiation or by any other suitable method.

EXAMPLE 13

Sterile Nonaqueous Parenteral Suspension

Crystalline ceftiofur hydrochloride (milled or micronized): 1 to 100 gms.
Chlorobutanol Anhydrous: 5.25 gms.
or
Benzyl Alcohol: 9.25 gms.
Corn Oil USP q.s. adjust: 1000 cc.
or
Cottonseed oil q.s. adjust: 1000 cc.

DIRECTIONS

Preservative is dissolved in sufficient oil to make 800 cc. Crystalline ceftiofur hydrochloride is added, and the suspension is colloid milled to a uniform consistency to break the aggregates. Add sufficient amount of oil to make 1000 mls. Stir and package into glass vials. The suspension can be sterilized by Cobalt 60 irradiation or sterile crystalline ceftiofur hydrochloride can be added to sterile vehicle and manufactured following aseptic procedure(s).

EXAMPLE 14

Sterile Extemporaneous Parenteral Suspension
(Nonaqueous Gel)-Controlled Release Formulation

| Sterile Vehicle Part I | 1000 |
|---|---|
| Benzyl Alcohol - preservative | 9.0 to 9.25 gms. |
| or | |
| Chlorobutanol | 5.0 to 5.25 gms. |
| Corn Oil Glyceryl Monostearate Gel | 1000 cc. |
| or | |
| Cottonseed Oil Glyceryl Monostearate Gel | 1000 cc. |
| Part II | 100 Vials |
| Crystalline ceftiofur hydrochloride (milled or micronized) | 1 to 100 gms. |

DIRECTIONS

Part I

Preservative is dissolved in sufficient gel, and the gel is filled into vials asceptically and the vials sealed. These vials will be packaged with the vials of Part II as companion package.

Part II 0.01 to 1.0 gm. of crystalline ceftiofur hydrochloride or sterilized crystalline ceftiofur hydrochloride is packaged in a sterile glass vial and the vials sealed. If the crystalline ceftiofur hydrochloride is non-sterile, then the packaged vials will be sterilized by Cobalt 60 irradiation.

Prior to dosing appropriate amounts of Part I diluent will be added to Part II sterile powder and shaken until homogeneous.

EXAMPLE 15

Sterile Extemporaneous Parenteral Suspension
(Nonaqueous)

| Sterile Vehicle Part I | 1000 |
|---|---|
| Benzyl Alcohol - preservative | 9.0 to 9.25 gms. |
| or | |
| Chlorobutanol | 5.0 to 5.25 gms. |
| Corn Oil, USP q.s. ad. | 1000 cc. |
| or | |
| Cottonseed Oil, USP q.s. ad. | 1000 cc. |
| Part II | 100 Vials |
| Crystalline ceftiofur hydrochloride, (milled and micronized) | 50 to 100 gms. |

Part I

Preservative is dissolved in the oil, and the solution sterilized by filtration. The sterile solution is filled into vials and the vials sealed. These vials will be packaged with the vials of Part II as companion package.

Part II 0.5 to 1.0 gm. of crystalline ceftiofur hydrochloride or sterilized crystalline ceftiofur hydrochloride is packaged in a sterile glass vial and the vials sealed. If the crystalline ceftiofur hydrochloride is non-sterile, then the packaged vials will be sterilized by Cobalt 60 irradiation.

Prior to dosing appropriate amounts of Part I diluent will be added to Part II sterile powder and shaken until uniformly mixed.

EXAMPLE 16

Suppositories

Formulation for a 2 gm. suppository containing 62.5 mg. of crystalline ceftiofur hydrochloride is given. However, any size suppository can be manufactured using any amount of ceftiofur hydrochloride and appropriate amounts of excipients at the same ratio as indicated below.

| | Lot Size 12 |
|---|---|
| Crystalline ceftiofur hydrochloride (milled or micronized) | 0.750 gm. |
| PEG-400 | 14.4 ml. |
| PEG-8000 | 9.6 gm. |

DIRECTIONS

Measure out 14.4 ml. of PEG-400 and place in a container suitable for heating. Add 9.6 gms. of PEG-8000 (melting point 140° F.) to the PEG-400 solution and melt over a hot water bath approximately two minutes or until there is a clear solution.

Add crystalline ceftiofur hydrochloride and stir until dispersed. Pour the mix into the mold and let set. Chill the mold. Remove suppositories after they set up 15–30 minutes at room temperature. Sterile suppositories can be manufactured with sterile raw materials and observing aseptic conditions during manufacturing, or can be sterilized by Cobalt 60 irradiation.

EXAMPLE 17

Suppositories

Suppositories can also be manufactured from excipients such as cocoa butter, Suppocire TM AM, Suppocire $AS_2$, and Suppocire AT, Suppocire BT or Suppocire CT brand of $C_8$ to $C_{10}$-saturated fatty acid glycerides.

Formula for a 2 gm. suppository containing 62.5 mg. of crystalline ceftiofur hydrochloride is given; however, any size suppository can be manufactured using any desired amount of crystalline ceftiofur hydrochloride, and appropriate amount of excipient.

| | Lot Size 12 |
|---|---|
| Crystalline ceftiofur hydrochloride (milled or micronized) Sterile | 0.750 gm. |
| Suppocire AM or $AS_2$, or AT, or BT or CT | 23.25 gm. |

DIRECTIONS

Weigh the Suppocire TM diluent in a container suitable for heating. Melt (45° C. temperature) over a hot water bath for approximately two minutes or until there is a clear solution (microwave oven can also be used instead of the water bath). Sterilize by filtration. Add sterile crystalline ceftiofur hydrochloride and stir until dispersed. Pour the mix into the cold mold. After two to four minutes, the surplus of the casting is eliminated by scraping. The temperature and time of cooling must be governed according to the type of formula. The circulating cold air should come in contact with all faces of the mold. Release from the mold must be gentle. Sterile suppositories can be manufactured with sterile raw materials and observing aseptic conditions during manufacturing, or can be sterilized by Cobalt 60 irradiation.

EXAMPLE 18

Capsules

One thousand two-piece hard gelatin capsules for oral use, each containing 50 mgs. of activity of crystalline ceftiofur hydrochloride, are prepared from the following types and amounts of materials:

|  | 1000 |
|---|---|
| Crystalline ceftiofur hydrochloride or | (50 gms.) |
| *Coated with Carnauba Wax ® or |  |
| *White Wax |  |
| Talc and/or | 75 gms. |
| Magnesium Stearate | 25 gms. |

( ) = Activity of ceftiofur hydrochloride
*Coated crystalline ceftiofur hydrochloride will have controlled release properties.
The materials are thoroughly mixed and then encapsulated in the usual manner. Different strength capsules can be prepared by changing the amounts of crystalline ceftiofur hydrochloride.

EXAMPLE 19

Tablets

One thousand compressed tablets for oral use, each containing an amount equivalent to 50 mgs. crystalline ceftiofur hydrochloride can be prepared using the following:

Ceftiofur hydrochloride crystalline: 50 gms.
Lactose: 375 gms.
Corn Starch: 65 gms.
Magnesium Stearate: 10 gms.

The ingredients are thoroughly mixed and slugged. The slugs are broken down by forcing through a screen. The resulting mixture is then compressed into tablets. Different strength tablets can be prepared by appropriate changes in the amounts of ceftiofur hydrochloride and the excipients.

STRUCTURE SHEET

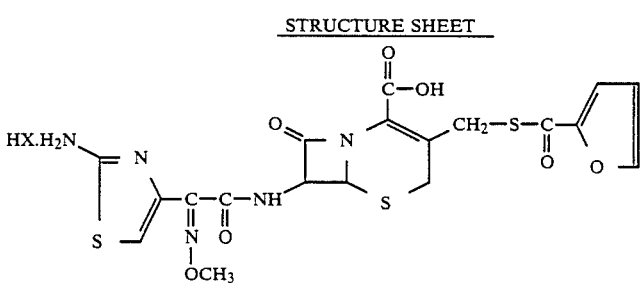

Formula (1)

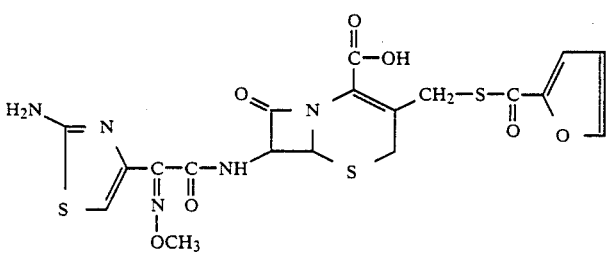

Formula (2)

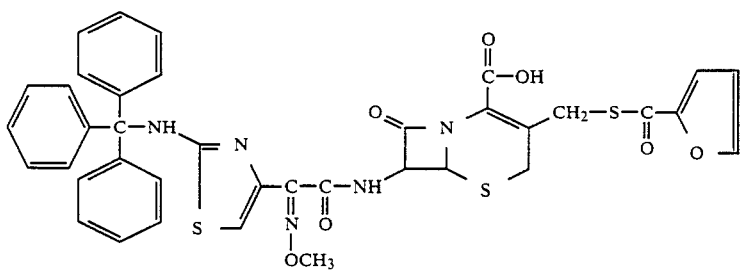

Formula (3)

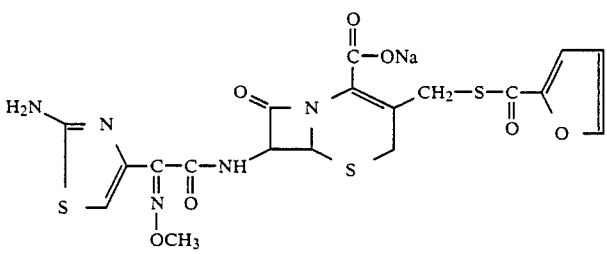

Formula (4)

We claim:
1. A cephalosporin hydrohalide compound of the formula

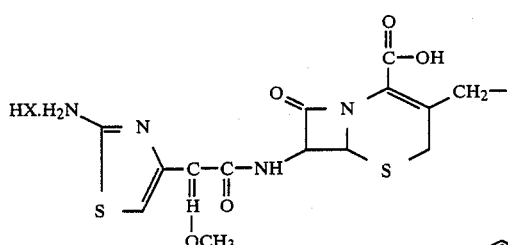

(1)

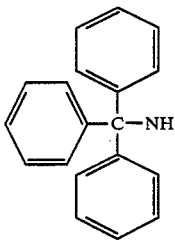

(2)

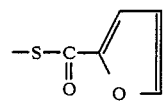

where X is chloride or bromide.

2. A compound according to claim 1 where X is chloride.
3. A crystalline compound according to claim 1.
4. A crystalline compound according to claim 2.
5. A compound according to claim 4 which has the following x-ray powder diffraction pattern when crystallized from an acetone/water mixture.

| interplanar d-spacings | intensity (relative %) |
|---|---|
| 18.4 | 44.2 |
| 12.4 | 73.1 |
| 8.26 | 50.0 |
| 7.82 | 100.0 |
| 7.69 | 17.9 |
| 6.19 | 48.1 |
| 5.86 | 32.1 |
| 5.21 | 23.1 |
| 5.12 | 40.4 |
| 4.74 | 30.1 |
| 4.37 | 21.8 |
| 4.23 | 13.5 |
| 3.98 | 26.9 |
| 3.91 | 35.9 |
| 3.81 | 17.9 |
| 3.30 | 14.1 |
| 3.01 | 12.8 |
| 2.88 | 14.1 |

6. A process for preparing a crystalline cephalosporin hydrohalide salt of the formula

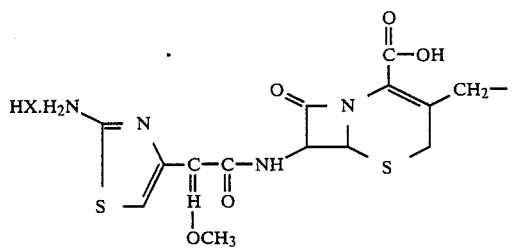

(1)

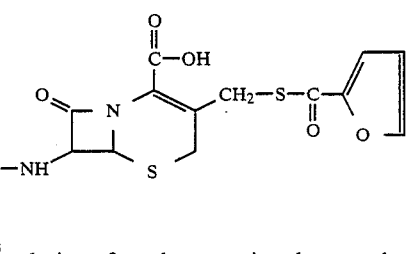

where X is chloride or bromide, which comprises the steps of
(a) treating the N-tritylamino cephalosporin compound of the formula (3)

with a solution of a polar organic solvent and water and hydrogen halide, where halide is chloride or bromide, in an amount which is at least stoichiometrically equivalent to the amount of the N-trityl compound (3) in the mixture,
(b) heating the mixture from step (a) to a temperature of at least 45° C. and for a time sufficient to effect detritylation,
(c) decreasing the concentration of the polar organic solvent in the aqueous phase of mixture from step (b) to effect formation of crystalline cephalosporin hydrohalide salt (1),
(d) separating the crystalline cephalosporin hydrohalide salt from the slurry mixture from step (c),
(e) washing the separated crystalline cephalosporin hydrohalide salt from step (d) with water and polar organic solvent, and drying the washed crystalline cephalosporin hydrohalide salt from step (e).

7. A process according to claim 6 wherein the crystalline cephalosporin hydrohalide salt of Formula 1 being prepared is the hydrochloride salt.
8. A process according to claim 7 wherein in step (c) of the process, toluene is used as the non-polar, water immiscible organic liquid to separate by-product trityl alcohol and to decrease the quantity of the polar organic liquid in the aqueous phase of the mixture.
9. A process according to claim 7 wherein step (c) of the process heptane is used as the non-polar, water immiscible organic liquid to separate trityl alcohol by-product and the mixture is distilled to remove polar organic liquid therefrom to enhance formation of the crystalline cephalosporin hydrochloride.
10. A pharmaceutical composition useful in pharmaceutically effective dosage unit form for alleviating the effects of undesired bacterial infections in warm-blooded mammals which comprises a compound according to claim 1 in combination with a pharmaceutically acceptable carrier.
11. A composition according to claim 10 wherein the compound is ceftiofur hydrochloride.
12. A method for alleviating the effects of undesired bacterial infections in a warm-blooded animal which comprises administering to an animal suffering such a bacterial infection an effective amount of a compound of claim 1 in a pharmaceutically acceptable dosage unit form.
13. A method according to claim 12 wherein the active compound is ceftiofur hydrochloride.

* * * * *

UNITED STATES PATENT AND TRADEMARK OFFICE

CERTIFICATE EXTENDING PATENT TERM
UNDER 35 U.S.C. § 156

PATENT NO.      :   4,902,683

ISSUED          :   February 20, 1990

INVENTOR(S)     :   Mahendra I. Amin et al.

PATENT OWNER    :   Pharmacia & Upjohn Company

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

460 days from February 20, 2007, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 15th day of July 1998.

Bruce A. Lehman
Assistant Secretary of Commerce and
    Commissioner of Patents and Trademarks